(12) United States Patent
Chandrasekhar et al.

(10) Patent No.: US 12,247,239 B2
(45) Date of Patent: Mar. 11, 2025

(54) CHEMO-ENZYMATIC PROCESS FOR THE PREPARATION OF HOMOPROPARGYLIC ALCOHOL

(71) Applicant: Council of Scientific and Industrial Research, New Delhi (IN)

(72) Inventors: Srivari Chandrasekhar, Telangana (IN); Subhash Ghosh, Telangana (IN); Avula Shiva Krishna, Telangana (IN); Chada Raji Reddy, Telangana (IN); Gangarajula Sudhakar, Telangana (IN); Kumaraguru Thenkrishnan, Telangana (IN); Srihari Pabbaraja, Telangana (IN); Prathama Satyendra Mainkar, Telangana (IN); Rajesh Nasam, Telangana (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 517 days.

(21) Appl. No.: 17/621,052

(22) PCT Filed: Jun. 17, 2020

(86) PCT No.: PCT/IN2020/050533
§ 371 (c)(1),
(2) Date: Dec. 20, 2021

(87) PCT Pub. No.: WO2020/255164
PCT Pub. Date: Dec. 24, 2020

(65) Prior Publication Data
US 2022/0333139 A1  Oct. 20, 2022

(51) Int. Cl.
| | |
|---|---|
| C12P 7/02 | (2006.01) |
| C12N 9/20 | (2006.01) |
| C12P 7/04 | (2006.01) |
| C12P 7/625 | (2022.01) |
| C12P 41/00 | (2006.01) |

(52) U.S. Cl.
CPC ............ *C12P 7/04* (2013.01); *C12N 9/20* (2013.01); *C12P 7/625* (2013.01); *C12P 41/002* (2013.01); *C12Y 301/01003* (2013.01)

(58) Field of Classification Search
None
See application file for complete search history.

(56) References Cited

U.S. PATENT DOCUMENTS

| | | | |
|---|---|---|---|
| 6,214,865 B1 | 4/2001 | Littlefield et al. | |
| 2009/0259058 A1 | 10/2009 | Henschke | |

FOREIGN PATENT DOCUMENTS

| | | |
|---|---|---|
| WO | 1995033845 A1 | 12/1995 |
| WO | 2000061777 A1 | 10/2000 |
| WO | 2005118565 A1 | 12/2005 |
| WO | 2006076565 A2 | 7/2006 |

OTHER PUBLICATIONS

Ranu et al., "Facile and Efficient Synthesis of Homoallylic Alcohols Using Allyl Bromide and Commercial Zinc Dust", Tetrahedron Lett. 36:4885-4888, 1995 (Year: 1995).*
Raminelli et al., "Kinetic resolution of propargylic and allylic alcohols by Candida antarctica lipase (Novozyme 435)", Tetrahedron: Asymmetry 15:3117-3122, 2004 (Year: 2004).*
Conde et al., Journal of Molecular Catalysis B: Enzymatic 7:299-306, 1999 (Year: 1999).*
Jõgi et al., Molecules 6:964-968, 2001 (Year: 2001).*
Journal of American Chemical Society, 1992, 114, pp. 3162-3164.
Jiang, et al., "A Novel Route to the F-Ring of Halichondrin D. Diastereoselection in Pd(0)-Mediated meso and $C_2$ Diol Desymmetrization", Organic Letters, vol. 4, No. 20, pp. 3411-3414, 2002.
Liu, et al., "Catalytic Enantioselective Cr-Mediated Propargylation: Application to Halichondrin Synthesis", Organic Letters, vol. 11, No. 20, pp. 4520-4523, 2009.
Trost, et al., "Ligand-accelerated Enantioselective Propargylation of Alsehydes via Allenzylzinc Reagents", Organic Letters, vol. 13, No. 08, pp. 1900-1903, 2011.
International Search Report in reference to co-pending Indian Patent Application No. PCT/IN2020/050533 filed Jun. 17, 2020.

* cited by examiner

Primary Examiner — David Steadman
(74) Attorney, Agent, or Firm — Dinsmore & Shohl LLP (57) ABSTRACT

The present invention relates to an enzymatic process for preparation of optically pure enantiomers of homopropargylic alcohol compounds of formula I, which are useful intermediates for the synthesis of Halichondrin B and analogs. wherein, P is H or an alcohol protecting group, n is an integer ranging from 0-12.

formula (I)

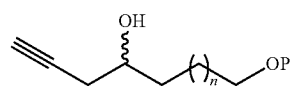

10 Claims, 2 Drawing Sheets

CHEMO-ENZYMATIC PROCESS FOR THE PREPARATION OF HOMOPROPARGYLIC ALCOHOL

CROSS REFERENCES TO RELATED APPLICATIONS

This application is a national-stage application under 35 U.S.C. § 371 of International Application No. PCT/IN2020/050533, filed Jun. 17, 2020, which International Application claims benefit of priority to Indian Patent Application number 201911024666, filed Jun. 21, 2019.

FIELD OF THE INVENTION

The present invention relates to a chemo-enzymatic process for the preparation of optically pure enantiomers of homopropargylic alcohol compound of formula I. Particularly, present invention relates to optically pure enantiomers of homopropargylic alcohol compound of formula I, useful intermediates for the preparation of halichondrin B and analogues such as Eribulin. More particularly, the present invention relates to optically pure enantiomer compounds of formula I i.e. I(a) and I(b), which are obtained by enzymatic resolution method.

Formula (I)

Formula (R)-I (a)

(a)

Formula (S)-I (b)

(b)

wherein, P is H or an alcohol protecting group;
n is an integer ranging from 0-12.

BACKGROUND OF THE INVENTION

Eribulin is a microtubule inhibitor indicated for the treatment of patients with metastatic breast cancer who have previously received at least two chemotherapeutic regimens for the treatment of metastatic disease. It is a structurally simplified, synthetic analog of halichondrin B. The mesylate salt of Eribulin is also known as Halaven® or E7389.

Methods and intermediates for the synthesis of Eribulin mesylate and other Halichondrin B analogs are described in International Publication Nos. WO 2005/1 18565, WO 2009/046308, WO 2009/064029, and WO 2009/124237; U.S. Pat. Nos. 6,214,865; 6,214,865 and Indian publication Nos. IN 02/2018; IN 07/2015; IN 47/2017 and IN 48/2017. New methods for the synthesis of halichondrin B analogs, in particular Eribulin, are desirable because of its important chemotherapeutic application.

A 4-methylene tetrahydrofuran compound of formula II is used as an intermediate (C14-C26 Building block) for the preparation of halichondrin B analogues such as Eribulin. Optically pure enantiomers of homopropargylic alcohol compound of formula I, (I(a) and I(b)) are used as key starting materials for the preparation of above said intermediate.

Processes for the preparation of a 4-methylene tetrahydrofuran compound of formula II have been disclosed in PCT application No. 2005/118565A1, J. Am. Chem. Soc, 1992, 114, 3162 and Org. Lett., 2002, 4, 3411-3414. The process for the preparation of racemic homopropargylic alcohol for the simple aldehyde was disclosed in Molecules 2001, 6, 964-968 with poor yield (25%). The processes for the preparation of optically pure homopropargylic alcohol compound of formula I disclosed in Org. Lett., 2009, 11, 4520-4523 by $CrBr_3$ mediated asymmetric propargylation of an aldehyde with a propargyl halide with 78% yield and 90% e.e. Further, the e.e was improved by enantioselective Amano lipase catalyzed hydrolysis of acetate (the reaction mixture was stirred in buffer (pH 7) at 50° C. for 43 h). It leads to the enzyme becoming soluble in buffer and impossible to reuse. It also leads to the emulsion formation during work-up and increase in the production cost. Another general process for the preparation of optically pure homopropargylic alcohol was disclosed in Org. Lett., 2011, 13, 1900-1903 mediated by $ZnEt_2$ and chiral amino alcohol ligand.

Thus, the reported processes suffer from major disadvantages, including use of highly expensive toxic metal-based reagents, low e.e, and large amounts of catalysts, cryogenic conditions, longer reaction time and using column chromatography for the isolation of products.

Hence, there remains a need to provide an alternative greener process for the preparation of optically pure homopropargylic alcohol compounds of formula I (a) & (b) which is simple, economic and industrially viable, which in turn can be converted to Eribulin. Herein, present invention provides an alternative chemo-enzymatic acylation process for the preparation of the above compounds in organic solvents and without column chromatography for the isolation of products. The enzyme was found to be highly recyclable. This recovery and re-use of the enzyme further reduces the cost and makes the process more economically viable.

OBJECTS OF THE INVENTION

Main objective of the present invention is to provide a chemo-enzymatic process for the preparation of optically pure enantiomers of homopropargylic alcohol compound of formula I.

Another objective of the present invention is to provide optically pure enantiomers of homopropargylic alcohol compound of formula I, useful intermediate for the preparation of halichondrin B and analogues such as eribulin.

Yet another objective of the present invention is to provide a process for the separation of optically pure enantiomer compounds of formula I i.e. Formula I(a) and Formula I(b) by enzymatic resolution method.

Yet another objective of the present invention is to provide a process for the separation of enantiomeric alcohol and its acylated enantiomer after enzymatic resolution without using column chromatography.

SUMMARY OF THE INVENTION

Accordingly, present invention provides a chemo-enzymatic process for preparation of optically pure enantiomers of homopropargylic alcohol compound of formula I

Formula (I)

(I)

wherein P is H or an alcohol protecting group;
n is an integer ranging from 0-12;
and the said process comprising the steps of:
  i. reacting aldehyde compound of formula (III) with propargyl halide compound of formula (IV) in an organic solvent in the presence of a metal catalyst to obtain racemic homopropargylic alcohol compound of formula I;

Formula (III)

Formula (IV)

≡⟶X wherein X=Cl, Br or I;
  ii. treating about 0.1 g/L to about 1000 g/L the racemic compound of formula I as obtained in step (i) with an enzyme in the presence of acyl donor and an organic solvent at temperature in the range of 20-50° C. to obtain a compound of formula I(a) and formula I(c);

Formula (R)-I(a)

Formula (S)-I(c)

iii. isolating the enantiomerically pure alcohol compound of formula I(a) and acetylated compound of formula I(c) using anhydride to obtain esters derivatives of formula I(d) from compounds formula I(a), while retaining the compound of formula I(c);

Formula (R)-I(d)

iv. washing the residues obtained from step (iii) with an organic solvent to obtain optically pure acetyl product compound of formula I (c);
  v. hydrolysing the compound of formula I (c) in presence of a base to obtain compound of formula I(b) by known method;

vi. hydrolysing the solid residue obtained from step (iv) with a base to obtain optically pure acetyl product compound of formula I (a).

In an embodiment of the present invention, the alcohol protecting group is selected from the group consisting of methoxymethyl ether (MOM-O—), 2-methoxyethoxymethyl ether (MEM-O—), tetrahydropyranyl ether (THP-O—), t-butyl ether, allyl ether, benzyl ether (Bn-O—), p-methoxy benzyl ether (—O-PMB), t-butyldimethylsilyl ether (TBDMS-O—), t-butyldiphenylsilyl ether (TBDPS-O—), acetic acid ester, pivalic acid ester or benzoic acid ester preferably t-butyldiphenylsilyl ether (TBDPS-O—).

In another embodiment of the present invention, metal catalyst used is selected from Zn dust or In preferably Zn dust.

In yet another embodiment of the present invention, acyl donor is selected from isopropenyl acetate and vinyl acetate.

In yet another embodiment of the present invention, organic solvents used in step (ii) and (iv) is selected from the group consisting of tetrahydrofuran, methyl 1-butyl ether, polar aprotic solvents selected from dimethyl sulfoxide and dimethyl formamide, ketones selected from acetone and methyl ethyl ketone, nitriles selected from acetonitrile and benzonitrile, alcohols selected from methanol, ethanol and t-butanol preferably methyl tert-butyl ether and toluene.

In yet another embodiment of the present invention, the enzyme used is lipases from *Pseudomonas* species selected from the group consisting of *Pseudomonas stutzeri*, Pseudomonas fluorescens, Pseudomonas cepacia or Burkholderia cepacia and Candida species selected from the group consisting of Candida rugosa, Candida cylindracea and Candida Antarctica.

In yet another embodiment of the present invention, loading of the enzyme in step (ii) is in the range of about 0.1 wt % to about 100 wt % with respect to the weight of substrate preferably about 0.1 wt % to about 10 wt % with respect to the weight of substrate.

In yet another embodiment of the present invention, the anhydride is selected from the group consisting of phthalic anhydride, maleic anhydride or succinic anhydride.

In yet another embodiment of the present invention, the enantiomeric purity of compounds of formula I (a) and I (b) obtained is in the range of 95 to >99%, preferably 99.99% e.e.

In yet another embodiment of the present invention, enzymes are packed in a column (Packed bed reactor, PBR) or in a fixed bed reactor and the reaction is carried out in a continuous flow process for a period in the range of 0.5 hr-6 hr (steady state).

DETAIL DESCRIPTION OF THE INVENTION

Present application relates to a chemo-enzymatic process for the preparation of optically pure enantiomers of homopropargylic alcohol compound of formula I

Formula (I)

(I)

wherein P is H or an alcohol protecting group;
n is an integer ranging from 0-12.

Present invention also relates to kinetic resolution of racemic homopropargylic alcohol into optically pure enantiomeric compound of formula I i.e. Formula I (a) and Formula I (b) by using enzymes.

Formula (R)-I (a)

Formula (S)-I (b)

wherein, P and n are same as above.

This homopropargylic alcohol substrate serves as useful intermediates for the preparation of halichondrin B and analogues such as Eribulin.

Figure 1:
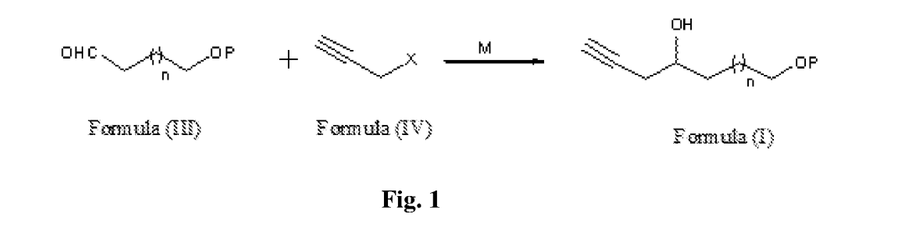
FIG. 1 represents process step for preparation of racemic-homopropargylic alcohol compound of formula (I).

The present application provides a process for preparation of optically pure enantiomers of homopropargylic alcohol compound of formula (I) comprising the steps of:

a) reacting aldehyde compound of formula III with propargyl halide compound of formula IV in an organic solvent in the presence of metal catalyst (M) to obtain racemic compound of formula I (FIG. 1)

Formula (III)

Formula (IV)

Figure 2:
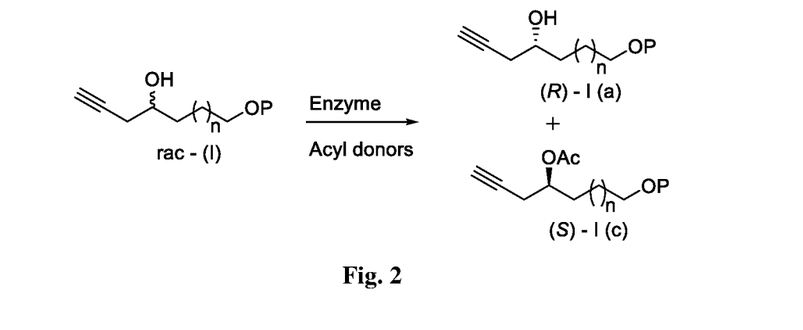
FIG. 2 represents process step for preparation of optically pure enantiomer compound of formula I i.e. I(a) and acylated enantiomer compound of formula I(c).
Figure 3:
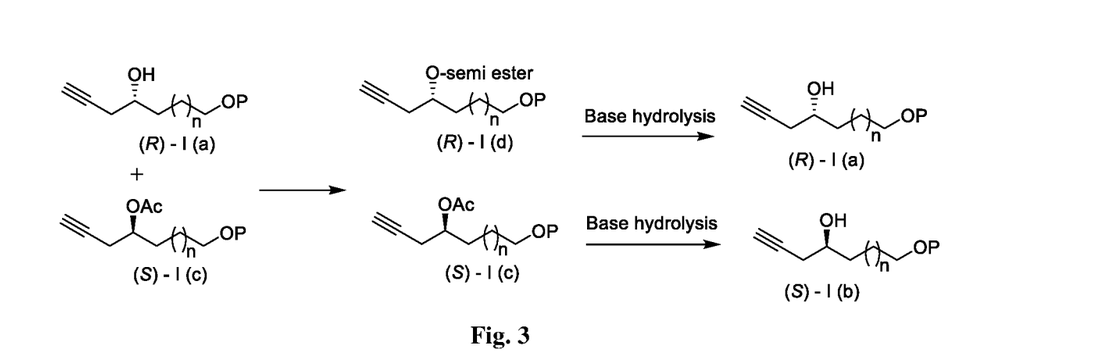
FIG. 3 represents process steps for the separation of enantiomer compound of formula I(a) and formula I (b) from formula I(a) and I(c).

≡—X wherein
P is H or an alcohol protecting group,
n is an integer ranging from 0-12,
X is a halogen selected from the group consisting of chlorine, bromine or iodine preferably bromine;
Metal catalyst (M) is selected from Zn dust or In, preferably Zn dust;

b) treating racemic compound of formula (I) with enzyme in presence of acyl donors and an organic solvent to obtain enantiomerically enriched alcohol of formula I (a) and optically pure acylated compound of formula I (c); (FIG. 2);

c) separating enantiomerically pure alcohol compound of formula I(a) and acetylated compound of formula I (c) by treating the mixture with anhydrides to obtain semi ester compound of formula I(d) from compound of formula I(a) while retaining the compound of formula I(c) (FIG. 3). Base hydrolysis of compound of formula I(d) and I(c) were carried out separately to obtain enantiomerically pure compounds of formula I(a) and I(b) (FIG. 3).

"Chemo-enzymatic" is defined as a chemical reaction wherein an enzyme is used as a catalyst.

The term "alcohol protecting group" refers to a group which temporarily masks the characteristic chemistry of a functional group because it interferes with another reaction. Preferred protecting groups include, without limitation, methoxymethyl ether (MOM-O—), 2-methoxyethoxymethyl ether (MEM-O—), tetrahydropyranyl ether (THP-O—), t-butyl ether, allyl ether, benzyl ether (Bn-O—), p-methoxy benzyl ether (—O-PMB), t-butyldimethylsilyl ether (TBDMS-O—), t-butyldiphenylsilyl ether (TBDPS-O—), acetic acid ester, pivalic acid ester, benzoic acid ester and the like. More specifically, the protecting group is t-butyldiphenylsilyl ether (TBDPS-O—).

The term 'immobilized enzymes' refers to enzymes physically confined or localized in a certain defined region of space with retention of their catalytic activities, and which can be used repeatedly and continuously. Immobilization can improve the stability of enzyme catalysts and protect their functional integrity in the harsh solvent environments and extreme temperatures characteristic of industrial and laboratory chemical processes (Hartmeier, W., Trends in Biotechnology 3: 149-153 (1985)). As used herein, the term enzyme immobilization refers to the insolubilization or enzyme catalyst by attachment to, encapsulation of, or by aggregation into crosslinked enzyme crystals (CLECs) and crosslinked enzyme aggregates (CLEAs).

The term "substituted" as used herein refers to substitution with any one or any combination of the following substituents: fluorine, chlorine, bromine and iodine; hydroxy; nitro; cyano; oxo (=O); thioxo (=S); azido; nitroso; amino; hydrazino; formyl; alkyl; alkoxy; aryl; haloalkyl groups such as trifluoromethyl, tribromomethyl and trichloromethyl; haloalkoxy groups such as —OCH$_2$Cl, —OCHF$_2$ and —OCF$_3$; arylalkoxy groups such as benzyloxy and phenylethoxy; cycloalkyl; —O-cycloalkyl; aryl; alkoxy; heterocyclyl; heteroaryl; alkylamino; —O—CH$_2$-cycloalkyl; —COOR$^a$; —C(O)R$^b$; —C(S)R$^a$; —C(O)NR$^a$R$^b$; —NR$^a$C(O)NR$^b$R$^c$; —N(R$^a$)SOR$^b$; —N(R$^a$)SO$_2$R$^b$; —NR$^a$C(O)OR$^b$; —NR$^a$R$^b$; —NR$^a$C(O)R$^b$—; NR$^a$C(S)R$^b$—; —SONR$^a$R$^b$—; —SO$_2$NR$^a$R$^b$; —OR$^a$; —OR$^a$C(O)OR$^b$—; —OC(O)NR$^a$R$^b$; OC(O)R$^a$; —OC(O)NR$^a$R$^b$—; —R$^a$NR$^b$R$^c$; —R$^a$OR$^b$—; —SR$^a$; —SOR$^a$ and —SO$_2$R$^a$; R$^a$, R$^b$ and R$^c$ each independently represents hydrogen atom; substituted or unsubstituted groups selected from alkyl; aryl; arylalkyl; cycloalkyl; heterocyclyl; heteroaryl and heteroarylalkyl; R$^a$, R$^b$ and R$^c$ are also combined to form a 3-7 membered ring having 0-2 hetero atoms.

The term "base" refers to the present invention is an organic or inorganic base, preferably selected from lithium hydroxide, sodium hydroxide, potassium hydroxide, sodium carbonate, potassium carbonate, sodium bicarbonate, potassium bicarbonate, triethylamine, tri-n-butylamine, sodium ethoxide, tBuOK, 1,5-diazabicyclo[4.3.0]-5-nonene, 1,8-diazabicyclo[5.4.0]-7-undecene, 4-methylmorpholine, 1-methylpiperidine, pyridine or N,N-dimethylaminopyridine.

The term "alkyl" refers to straight or branched aliphatic hydrocarbon groups having the specified number of carbon atoms, which are attached to the rest of the molecule by a single atom. Preferred alkyl groups include, without limitation, methyl, ethyl, n-propyl, isopropyl, butyl, isobutyl, t-butyl, pentyl, hexyl, heptyl, octyl and the like.

"Enantiomeric purity" of a compound is measured in terms of "enantiomeric excess" (e.e.) of the compound. "Enantiomeric excess" denotes the degree to which a compound contains one enantiomer in greater amounts than the other. The enantiomeric excess (e.e.) of a compound is calculated by the following formula:

e.e.=((R—S)/(R+S))×100; wherein, R and S stand for the individual optical isomer in the mixture (and R+S=1).

Acyl donors are acetyl donors or mono halo acetyl donors or optionally substituted phenyl esters. Acyl donors can be "reversible" or "irreversible" donors. Reversible donors include ethyl acetate and triacetin. Specific examples of acyl donors include isopropenyl acetate, triacetin, vinyl acetate, ethyl acetate, diacetin, ethylene glycol diacetate, cis-1,4-diacetoxy butane, 1,4-diacetoxy butane, phenyl acetate, 1,2,4-triacetoxy benzene, 1,3-butanedial diacetate, 1,2-propanediol diacetate, n-butyl acetate, triethylene glycol diacetate, isopropyl acetate, and isobutyl acetate, and the like. More preferred acyl donors are Trifluoroethyl butyrate, S-ethylthiooctanoate, biacetyl mono-oxime acetate, vinyl acetate, isopropenyl acetate, 1-ethoxyvinyl acetate, diketene, acetic acid anhydride, succinic acid anhydride, isobutyric anhydride.

Anhydride is selected from the group consisting of phthalic anhydride, maleic anhydride or succinic anhydride.

Isolation of compounds of formula I (a) and I (c) and/or I (c) and I (d) were involving the use of any method known in the existing art i.e. by crystallization or by acid base work-up.

The molar ratio of acyl donor to alcohol can be 0.5:2 for racemic alcohols, i.e. 0.5 equivalents for the quantitative reaction of one enantiomer. Alternatively, the acyl donor may also be employed in a large excess, for example a 100-fold molar excess in situations when, for example, low amounts of enzyme are to be used. Preferred stoichiometries are between about 1 and about 10 equivalents of the acyl donor to the alcohol.

The concentration of substrate for the chemo-enzymatic process of the present application may be from about 0.1 g/L to about 1000 g/L. The loading of the enzyme, for the chemo-enzymatic process of the present application, may be from about 0.1 wt % to about 100 wt % with respect to the weight of substrate. Specifically, the loading of the enzyme, for the chemo-enzymatic process of the present application, may be less than about 10 wt % with respect to the weight of substrate.

The enzymes employed in the present invention are lipases which are commercially available. Particularly preferred lipases include the lipases from *Pseudomonas* sp. such as *Pseudomonas stutzeri, Pseudomonas fluorescens, Pseudomonas cepacia* and *Burkholderia cepacia;* lipase from *Candida* species such as *Candida rugosa, Candida cylindracea* and *Candida antarctica.*

More specifically, the chemoenzymatic process of the present application may be performed using lipase from *Pseudomonas fluorescens.*

The enzyme can be employed in free form or immobilized form. Methods for immobilizing enzymes are well known to those of skill in the art. A column process may be used for both free and immobilized enzymes. The quantity of enzyme is selected as a function of the size of the batch, of the reactivity of the alcohol, of the desired reaction time, and of the free or immobilized nature of the enzyme. Determining the quantity of enzyme is readily carried by simple preliminary experiments where the reaction is carried out on a pilot scale.

It is preferred that the solution be stirred during the reaction. The reaction time varies, depending on the nature of the alcohol employed and on the amount of enzyme and solvent, and is usually only a few hours, but may be up to 2 weeks. Progress of the reaction is conveniently carried out using any method known to those skilled in the art of organic synthesis, including thin layer chromatography (TLC) and HPLC.

The chemo-enzymatic process of the present application may be carried out in a suitable organic solvent or in a mixture of solvents or without organic solvents. The organic solvent may include but not limited to ethers such as diisopropyl ether (DIPE), 2-Methyltetrahydrofuran, tetrahydrofuran (THF), methyl tert-butyl ether and the like; polar aprotic solvents such as dimethyl sulfoxide, dimethylformamide and the like; ketones such as acetone and the like, nitriles such as acetonitrile and the like; alcohols such as methanol, ethanol, tert-butanol and the like. Alternatively, the chemo-enzymatic process of the present application may be carried out in a mixture of alcohol and organic solvents.

Examples of other suitable organic solvents include but not limited to cyclohexane (CH), 1,4-dioxane, heptane, hexane, dimethyl carbonate (DMC), Methyl isobutyl ketone (MIBK), ethyl acetate, chloroform, 1,2-dichloroethane, toluene, xylene and the like. More specifically, the organic solvents used are preferably nonpolar, and preferably are ethers, such as diisopropyl ether or t-butyl methyl ether (MTBE), or hydrocarbons such as isohexane, pentane, heptane or hexane.

The chemo-enzymatic process of the present application may be carried out at a suitable temperature. Specifically, the temperature may be of about −10° C. to about the boiling point of the solvent; more specifically of about −10° C. to about 80° C. and more specifically of about 15° C. to about 40° C.

The chemo-enzymatic process of the present application may be carried out in presence of a stabilizer or additives. Any stabilizer or additives are known in the art may be used for the above chemo-enzymatic process of the present application.

The chemo-enzymatic process of the present application may be carried out in suitable equipment, for example, in a closed reaction vessel made of glass or metal or bioreactors or in a packed bed reactors.

The chemo-enzymatic process of the present application may be carried out under an atmosphere of nitrogen or air.

The compounds of formula (I) and its isomers may be isolated from the suspension by methods known in the art.

Compounds disclosed herein may exist as single stereoisomers, racemates and or mixtures of enantiomers and/or diastereomers. All such single stereoisomers, racemates and mixtures thereof are intended to be within the scope of the subject matter described.

This invention, in addition to the above listed compounds, is intended to encompass the use of analogs of such compounds. In this context and analogs are molecules having substantial biological similarities regardless of structural similarities.

Detail of the Biological Resources Used

Lipases from *Pseudomonas* sp. are procured from Amano Pharmaceuticals, Nagoya, Japan and lipases from *Candida* species are procured from Novozyme 435, M/s Novozymes, Denmark.

EXAMPLES

The following examples are given by way of illustration and therefore should not be construed to limit the scope of the invention.

Example 1: Preparation of Rac-Homopropargylic Alcohol of Formula I

To a stirred solution of aldehyde of formula III (wherein n=1 and P=TBDPS) (100 g, 306 mmol) in dry THF (750 ml) propargyl bromide (79.2 ml, 919 mmol) was added followed by activated Zn dust (80 gr. 61.32 mmol) at −20° C., then after that saturated ammonium chloride was added slowly drop wise until effervesces were stopped. After completion of the reaction (monitored by TLC) the crude was filtered through celite bed and the filtrate was concentrated under reduced pressure. The crude residue was extracted with ethyl acetate (2×500 mL) and the combined organic extracts were washed with brine, dried over anhydrous $Na_2SO_4$ and evaporated under reduced pressure to furnish racemic alcohol I (wherein n=1 and P=TBDPS) (108 g, 95.9%).

Example 2: Screening of Enzymes for Selective Acylation

To a solution of (+/−)-homopropargylic alcohol I (wherein n=1 and P=TBDPS) (50 mg, 0.136 mmole) in MTBE (1 mL) and isopropenyl acetate (0.015 mL), enzyme (10 mg) was added. The reaction mass was kept for shaken at 27° C. for 10 hrs. The reaction mixture was analysed from HPLC to check the conversion and e.e. (−)-represents no conversion.

| S. No | Enzymes | Conversion (%) | e.e (%) |
|---|---|---|---|
| 1 | Rhizopus arrhizus | <2 | — |
| 2 | Rhizopus niveus | <2 | — |
| 3 | Porcine Pancreas | <2 | — |
| 4 | Candida cylindracea | 17 | 4 |
| 5 | hog pancreas | — | — |
| 6 | Immobilized Lecitase Ultra ® | — | — |
| 7 | Candida rugosa | <3 | NA |
| 8 | Wheat germ | — | — |
| 9 | Pseudomonas fluorescens | 50 | >99 |
| 10 | Candida antarctica (CAL-B), | 29 | 35 |
| 11 | Thermomyces lanuginosus | <2 | NA |

Example 3: Screening of Solvents for Acylation Using Enzymes

To a solution of rac-homopropargylic alcohol I (wherein n=1 and P=TBDPS) (50 mg, 0.136 mmol) in organic solvents (1 mL) and isopropenyl acetate (0.015 mL) enzyme (10 mg) was added. The reaction mass was kept for shaken at 27° C. for 10 hrs. The reaction mixture was analysed from HPLC to check the conversion and e.e.

| | Candida antarctica (CAL-B) | | Pseudomonas fluorescens | |
|---|---|---|---|---|
| Solvents | Conversion | ee% | Conversion | ee% |
| MTBE | 28.50 | 34.77 | 50 | >99 |
| Toluene | 28.42 | 34.79 | 1.87 | 2.60 |
| DIPE | 13.63 | 5.61 | 11.48 | 7.96 |
| MIBK | 0 | 0.67 | 5.41 | 4.2 |
| Cyclo hexane | 11.58 | 10 | 10.96 | 8.71 |
| ACN | 1.24 | 2.22 | 8.66 | 7.2 |
| t-BuOH | 9.72 | 9.38 | 28.32 | 31.7 |
| DMC | 0 | 1.84 | 0 | 2.7 |
| 1,4-Dioxane | 0 | 0.58 | 2.76 | 1.84 |

Figure 4:
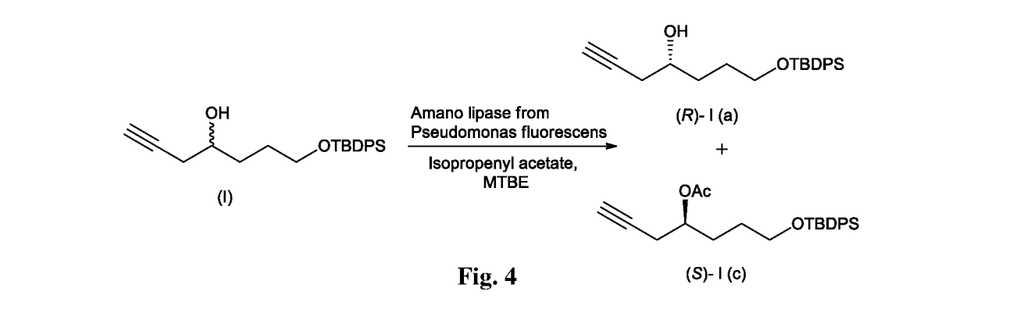
FIG. 4 represents process step for preparation of compound I (a) and I (c) as in example 4.

Example 4: Preparation of Compound I (a) and I (c) (FIG. 4)

To a 25 mL round-bottomed flask with a stir bar the rac-homopropargylic alcohol I (wherein n=1 and P=TBDPS) (1 g, 2.72 mmol), isopropenyl acetate (0.32 mL, 2.99 mmol), MTBE (10 mL), and Lipase from *Pseudomonas fluorescens* (0.1 g) were added. The reaction mixture was stirred at 27° C. for 16 hr. The progress of the reaction was monitored by TLC. The optical purity of homopropargylic alcohol and acetate thus obtained was confirmed to be >99.99% from chiral HPLC analysis. The optical purity of acetate was checked after deprotection.

Figure 5:
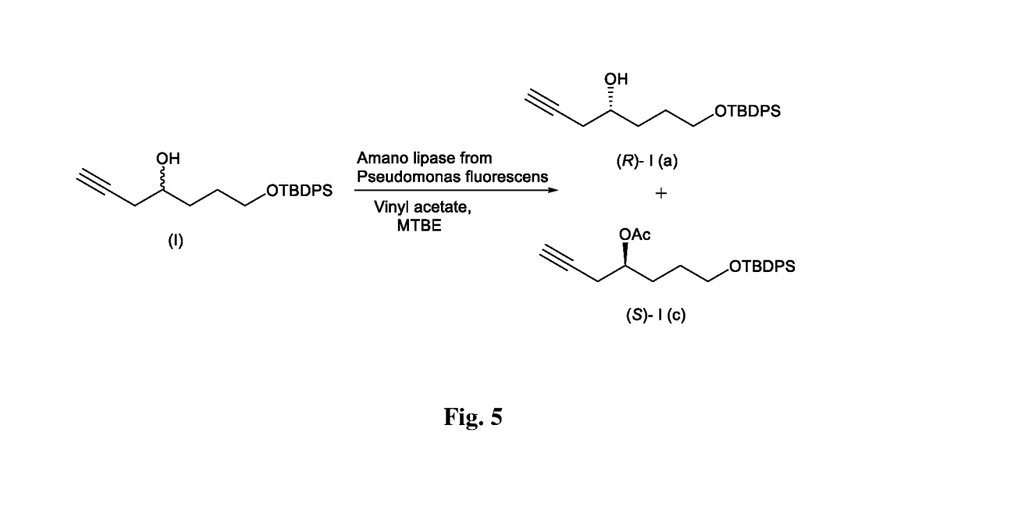
FIG. 5 represents process step for preparation of compound I (a) and I (c) as in example 5.

Example 5: Preparation of Compound I (a) and I (c) (FIG. 5)

To a 25 mL round-bottomed flask with a stir bar the (+/−)-homopropargylic alcohol I (wherein n=1 and P=TBDPS) (1 g, 2.72 mmol), vinyl acetate (0.28 mL, 3 mmol), MTBE (10 mL), and Lipase from *Pseudomonas fluorescens* (0.1 g) were added. The reaction mixture was stirred at 27° C. for 16 h. The progress of the reaction was monitored by TLC. The optical purity of homopropargylic alcohol I(a) and acetate I(c) thus obtained was confirmed to be >99.99% from chiral HPLC analysis. The optical purity of acetate was checked after deprotection.

Example 6: Preparation of Compound I (a) and I(c) (FIG. 4)

To a stirred solution of (+/−)-homopropargylic alcohol I (wherein n=1 and P=TBDPS) (100 g, 272.4 mmol) in MTBE (1.5 ltr), isopropenyl acetate (32 mL, 299.7 mmol), Lipase from *Pseudomonas fluorescens* (10 g) were added. The reaction mixture was stirred at 27° C. for 16 h. The progress of the reaction was monitored by TLC. After completion of the reaction, the enzyme was filtered and reused. The filtrate was concentrated and purified by column chromatography to obtain optically pure alcohol I (a): (48 g, yield 48%) and optically pure acylated compound I (c): 52 g, yield 47%. The optical purity of homopropargylic alcohol I (a) was confirmed to be >99.99% from chiral HPLC analysis. The optical purity of acetate was checked after deprotection.

Example 7: Deprotection of Acetate I (c) to Obtain Alcohol Compound I (b)

To a stirred solution of optically pure acetate of (S)-homopropargylic alcohol obtained from example 6 (52 g, 127.4 mmol) in MeOH (1 ltr) was sequentially added $K_2CO_3$ (17.57 g, 127.4 mmol) at 27° C. Then the reaction mixture was allowed to stirring for 4 hr after completion of the reaction (monitored by TLC) the reaction mixture was filtered and organic layer was evaporated to give crude mass that was dissolved in ethyl acetate (400 mL) and it was washed with water (100 mL) and brine (100 mL). Solvent was evaporated under reduced pressure to obtain optically pure (S)-homopropargylic alcohol (45.5 g, 97.6% yield & >99% e.e).

Example 8: Preparation of Optically Pure Homopropargylic Alcohol

Step 1: Enzymatic Acylation

To a 250 mL round-bottomed flask with a stirrer bar was added the (+/−) homopropargylic alcohol I (wherein n=1 and P=TBDPS) (10 g, 27.2 mmol), isopropenyl acetate (3.2 mL, 29.9 mmol), MTBE (100 mL), and Lipase from *Pseudomonas fluorescens* (1 g). The reaction mixture was stirred at 27° C. for 16 hr. The progress of the reaction was monitored by TLC.

Step 2: Esterification of Alcohol with Succinic Anhydride

After completion of enzymatic reaction, organic layer was filtered and washed the enzyme with MTBE (2×5 mL). The combined MTBE fraction obtained was evaporated under reduced pressure. The residue was diluted with DCM (100 mL) and treated with $Et_3N$ (5.89 mL, 40.86 mmol), succinic anhydride (1.49 g, 14.98 mmol) and DMAP (332 mg, 2.7 mmol) at 0° C. The reaction mixture was stirred at 27° C. for 16 h.

Step 3: Isolation of Unreacted Acetyl Product by Solvent Washing

After completion of the semi ester formation, the reaction mixture was evaporated under reduced pressure. The residue was washed twice with hexane (2×15 mL) to obtain optically pure acetyl product after evaporated under reduced pressure (5.1 g, 45.9% yield; >99.9% e.e, >99% e.e). The optical purity of acetate was checked after deportation.

Step 4: Isolation of Hydroxy Product by Base Hydrolysis

The residue obtained from step-3 was diluted with water and basified with 4N NaOH till pH reaches 12 and stirred for 1 hr. The reaction progress was monitored by TLC. After complete hydrolysis of semi-ester, the reaction mixture was extracted twice with EtOAc (2×50 mL). The organic layer was dried over anhydrous $Na_2SO_4$ and concentrated under reduced pressure to give an isolated optically pure homopropargylic alcohol (4.8 g, 48% yield, >99.99% e.e).

Step 5: Enzyme Recyclability

After 16 h of reaction (>49% conversion & >99% e.e), the enzyme was separated by filtration and washed twice with MTBE (15 mL). The combined organic portion was collected separately. The used enzyme was found to be recyclable for up to 10 times without significant change in productivity and activity of the enzyme. The recovered enzyme was used for next batch.

Example 9

Preparation of Optically Pure Homopropargylic Alcohol

Step 1: Enzymatic Acylation

To a 250 mL round-bottomed flask with a stirrer bar was added the (+/−)-homopropargylic alcohol I (wherein n=1 and P=TBDPS) (10 g), isopropenyl acetate (3.2 mL), MTBE (100 mL), and Lipase from *Pseudomonas fluorescens* (1 g). The reaction mixture was stirred at 27° C. for 16 h. After completion of the resolution, the enzyme was filtered and washed with MTBE (2×20 mL).

Step 2: Esterification of Alcohol with Succinic Anhydride

To the combined MTBE fraction (140 mL) obtained above was charged with $Et_3N$ (5.89 mL), Succinic anhydride (1.49 g) and DMAP at 0° C. The reaction mixture was stirred at 27° C. for 16 h.

Step 3: Isolation of Unreacted Acetyl Product by Solvent Wash

After completion of the semester formation, the semi-ester product was precipitated as white solid. The MTBE layer was filtered and washed twice with MTBE (2×5 mL) and combined organic layer was evaporated under reduced pressure to obtain acetyl product (5.03 g, 45.2% yield, >99% e.e). The optical purity of acetate was checked after deportation.

Step 4: Isolation of Hydroxy Product by Base Hydrolysis

The solid precipitate obtained from step-3 was diluted with water and basified with 4N NaOH till pH reaches 12 and stirred for 1 h. The reaction progress was monitored by TLC. After complete hydrolysis of semi-ester, the reaction mixture was extracted twice with EtOAc (2×5 mL). The organic layer was dried over anhydrous $Na_2SO_4$ and concentrated under reduced pressure gave an isolated optically pure homopropargylic alcohol (4.6 g, 46% yield; >99.9% e.e).

Example 10

Enzymatic Reaction in Packed Bed Reactor

Figure 6:
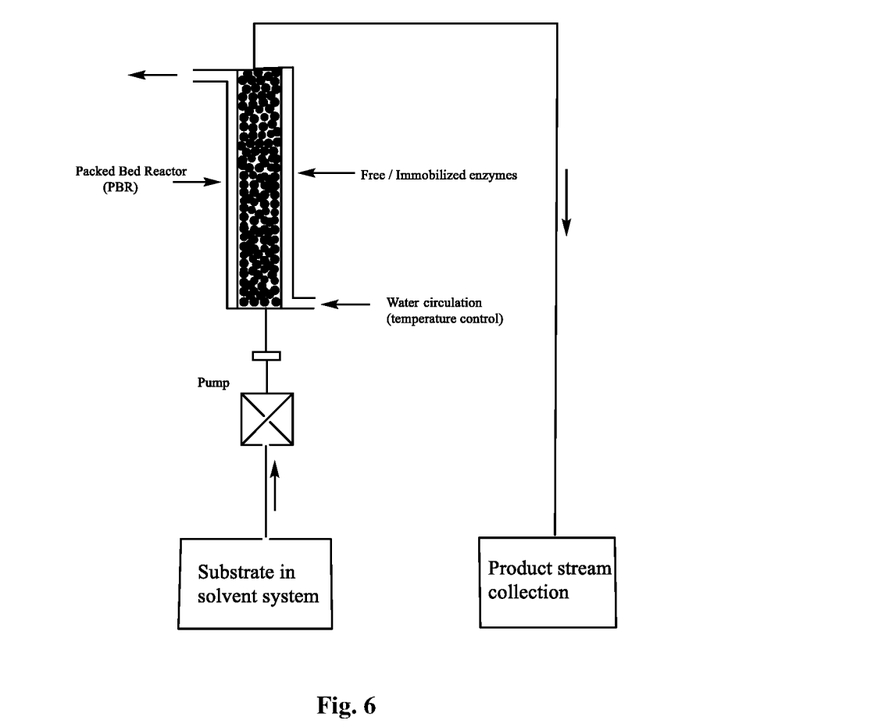
FIG. 6 represents schematic representation of Packed bed reactor (PBR).

The flow chemistry set-up, as illustrated in FIG. 6 was built using an empty HPLC column (250 mm×4 mm) which was filled with the Lipase from *Pseudomonas fluorescens* (2 g). (+/−)-homopropargylic alcohol I (wherein n=1 and P=TBDPS) (2 g, 10% w/v) and vinyl acetate (1 mL) dissolved in MTBE was then pumped at a fixed flow rate from the bottom of the reactor using an HPLC pump (Shimadzu LC 20AD) with 0.1 mL/min flow rate. The product stream was collected from top and analyzed by HPLC at steady state (30 mins). The optical purity of homopropargylic alcohol formula I (a) and acetate I (c) thus obtained was confirmed to be >99.99% from chiral HPLC analysis. The optical purity of acetate was checked after deprotection.

ADVANTAGES OF THE INVENTION

The various advantages of the present process are given below:
1. The present process serves as a highly efficient and scalable production method for the preparation of optically pure homopropargylic alcohol intermediates for the synthesis of Halichondrin B and analogs such as Eribulin.
2. This invention involves a process for the separation of optically pure homopropargylic alcohol intermediates by enzymatic resolution method.
3. Isolation and/or purification of the product/s is straight forward with high yields and purity.
4. Another advantage of the present invention is that the process provides novel method of isolation of pure compounds without the use of column chromatography.
5. This is an attractive and economic method for the production of optically pure homopropargylic alcohol intermediates.
6. This process could be adopted to generate a large library of process intermediates and optically pure homopropargylic alcohol intermediates, which have large applications in synthetic chemistry.
7. The enzymatic reaction carried out in a Packed bed reactor to improve the productivity and enzyme recyclability (cost improvement) by avoiding the attrition of enzyme compared to conventional stirred tank reactor.

The invention claimed is:
1. A chemo-enzymatic process for preparing optically pure enantiomers of a homopropargylic alcohol compound, the process comprising:
(i) reacting an aldehyde compound of formula (III):

(III)

where:
P is hydrogen or an alcohol protecting group; and
n is an integer from 0 to 12,
with a propargyl halide compound of formula (IV):

(IV)

where X is Cl, Br, or I;
in an organic solvent in the presence of a metal catalyst to obtain a racemic homopropargylic alcohol compound of formula (I);

(I)

where P and n are as defined in formula (III);
(ii) treating the racemic homopropargylic alcohol compound obtained in (i) with an enzyme, wherein the enzyme is a lipase from *Pseudomonas fluorescens, Candida cylindracea*, or *Candida Antarctica*, in the presence of an acyl donor and an organic solvent at temperature from 20° C. to 50° C. to obtain an enantiomerically enriched alcohol compound of formula (Ia):

(Ia)

where P and n are as defined in formula (III), and an optically pure acylated compound of formula (Ic):

(Ic)

where P and n are as defined in formula (III);
(iii) isolating the enantiomerically enriched alcohol compound of formula (Ia) and the optically pure acylated compound of formula (Ic) with an anhydride to obtain semi-ester derivatives having formula (Id) from the enantiomerically enriched alcohol compound of formula (Ia):

(Id)

where P and n are as defined in formula (III), while retaining the compound of formula (Ic);
(iv) washing the semi-ester derivatives of formula (Id) obtained from (iii) with an organic solvent to obtain an optically pure acetyl product having formula (Ic);
(v) hydrolysing the optically pure acylated compound of formula (Ic) in the presence of a base to obtain a compound of formula (Ib):

(Ib)

where P and n are as defined in formula (III); and
(vi) hydrolysing the semi-ester derivative of formula (Id) of (iii) with a base to obtain an optically pure enantiomerically enriched alcohol product having formula (Ia).

2. The process according to claim 1, wherein the alcohol protecting group is selected from the group consisting of methoxymethyl ether, 2-methoxyethoxymethyl ether, tetrahydropyranyl ether, t-butyl ether, allyl ether, benzyl ether, p-methoxybenzyl ether, t-butyldimethylsilyl ether, t-butyldiphenylsilyl ether, acetic acid ester, pivalic acid ester, and benzoic acid ester.

3. The process according to claim 1, wherein the alcohol protecting group is t-butyldiphenylsilyl ether.

4. The process according to claim 1, wherein the metal catalyst in (i) is zinc dust or indium.

5. The process according to claim 1, wherein the acyl donor in step (ii) is isopropenyl acetate or vinyl acetate.

6. The process according to claim 1, wherein the organic solvents in (ii) and (iv) are selected from the group consisting of tetrahydrofuran, methyl 1-butyl ether, dimethyl sulfoxide, dimethyl formamide, acetone, methyl ethyl ketone, acetonitrile, benzonitrile, methanol, ethanol, t-butanol, methyl tert-butyl ether, and toluene.

7. The process according to claim 1, wherein the enzyme in (ii) is loaded at from 0.1 wt. % to 100 wt. % with respect to the weight of the racemic homopropargylic alcohol compound.

8. The process according to claim 1, wherein the anhydride in (iii) is selected from the group consisting of phthalic anhydride, maleic anhydride, and succinic anhydride.

9. The process according to claim 1, wherein the compounds of formula (Ia) and formula (Ib) are obtained in at least 95% enantiomeric excess.

10. The process according to claim 1, wherein the enzyme in (ii) is packed in a column or in a fixed bed reactor, and wherein the reaction in (ii) is carried out as a continuous-flow process for 0.5 hours to 6 hours at steady state.

* * * * *